United States Patent [19]

Yamamoto et al.

[11] 4,148,796
[45] * Apr. 10, 1979

[54] γ-PIPERIDINOBUTYROPHENONES

[75] Inventors: Hisao Yamamoto, Nishinomiya; Masaru Nakao; Kikuo Sasajima, both of Toyonaka; Isamu Maruyama, Minoo; Shigenari Katayama, Takarazuka, all of Japan

[73] Assignee: Sumitomo Chemical Company, Limited, Osaka, Japan

[*] Notice: The portion of the term of this patent subsequent to Mar. 26, 1991, has been disclaimed.

[21] Appl. No.: 388,561

[22] Filed: Aug. 15, 1973

Related U.S. Application Data

[63] Continuation-in-part of Ser. No. 124,522, Mar. 15, 1971, Pat. No. 3,799,932.

[51] Int. Cl.² .................. C07D 401/04; C07D 211/50
[52] U.S. Cl. .................................. 546/199; 424/267; 546/221; 546/235; 546/237
[58] Field of Search ........... 260/293.6, 293.77, 293.79, 260/293.8

[56] References Cited

U.S. PATENT DOCUMENTS

| | | | |
|---|---|---|---|
| 3,161,645 | 12/1964 | Janssen | 260/293.4 |
| 3,438,991 | 4/1969 | Janssen | 260/294.7 |
| 3,462,444 | 8/1969 | Beckett et al. | 260/294.7 |
| 3,799,932 | 3/1974 | Yamamoto et al. | 260/293.6 |

*Primary Examiner*—Natalie Trousof
*Assistant Examiner*—Robert T. Bond
*Attorney, Agent, or Firm*—Stevens, Davis, Miller & Mosher

[57] ABSTRACT

Novel γ-piperidinobutyrophenone derivatives of the formula,

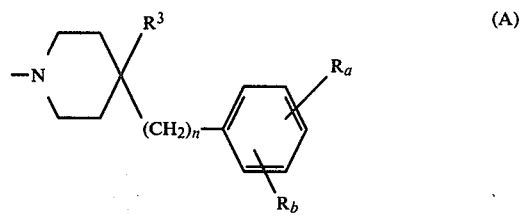

wherein
$R^1$ is halogen, amino, alkanoylamino, alkylamino or N-(alkanoyl)alkylamino;
$R^2$ is hydrogen or halogen, provided that when $R^1$ is halogen, $R^2$ must be halogen; and
Z is a piperidino group having the formula (A),

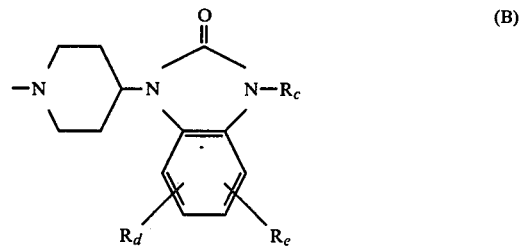

(wherein each of $R_a$ and $R_b$ is hydrogen, halogen, lower alkyl, lower alkoxy or trifluoromethyl; $R^3$ is hydrogen or hydroxyl; and n is 1 or 2), or a piperidino group having the formula (B),

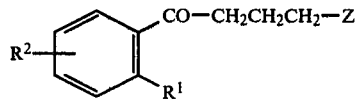

(wherein $R_c$ is hydrogen or lower alkyl; and each of $R_d$ and $R_e$ is hydrogen, halogen, lower alkyl or lower alkoxy), provided that when $R^1$ is amino and $R^2$ is hydrogen, Z cannot be represented by the formula (A), and their pharmaceutically acceptable acid addition salts, which are useful as psychotropic, neuroleptic or analgesic agents.

15 Claims, No Drawings

γ-PIPERIDINOBUTYROPHENONES

CROSS REFERENCE TO RELATED APPLICATIONS

This is a continuation-in-part of co-pending application Ser. No. 124522 filed on Mar. 15, 1971, now U.S. Pat. No. 3,799,932.

The present invention relates to novel butyrophenone derivatives, including pharmaceutically acceptable salts thereof and to pharmaceutical use of the same. More particularly, the compounds provided by the invention are γ-piperidinobutyrophenone derivatives represented by the formula,

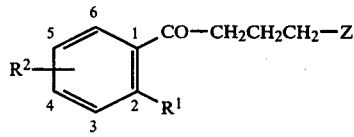

wherein
$R^1$ is halogen, amino, $C_1$–$C_5$ alkanoylamino, $C_1$–$C_4$ alkylamino or N-($C_1$–$C_5$8c -alkanoyl)-$C_1$–$C_4$ alkylamino; 10
$R^2$ is hydrogen or halogen, provided that when $R^1$ is halogen, $R^2$ must be halogen; and
Z is a piperidino group having the formula (A0,

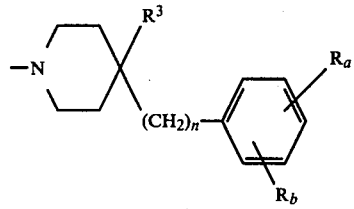

(wherein each of $R_a$ and $R_b$ is hydrogen, halogen, $C_1$–$C_4$ alkyl, $C_1$–$C_4$ alkoxy or trifluoromethyl; $R^3$ is hydrogen or hydroxyl; and n is 1 or 2), or a piperidino group having the formula (B),

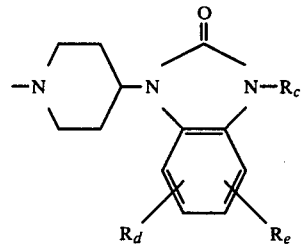

(wherein $R_c$ is hydrogen or $C_1$–$C_4$ alkyl; and each of $R_d$ and $R_e$ is hydrogen, halogen, $C_1$ –$C_4$ alkyl or $C_1$–$C_4$ alkoxy), provided that when $R^1$ is amino and $R^2$ is hydrogen, Z cannot be represented by the formula (A).

As used herein, $C_1$–$C_4$ alkyl or $C_1$–$C_4$ alkoxy may be straight or branched-chain radicals, such as, for example, methyl, ethyl, n-propyl, isopropyl, n-butyl, isobutyl, tertiary butyl and the like, and respectively, methoxy, ethoxy, propoxy, isopropoxy and the like, $C_1$–$C_5$ alkanoyl may also be straight or branched-chain radicals, such as, for example, formyl, acetyl, propionyl, butyryl, valeryl, isobutyryl, isovaleryl and the like, and halogen includes fluorine, chlorine, bromine and iodine.

The organic bases of this invention form pharmaceutically useful non-toxic salts with a variety of inorganic and organic acids including sulfuric, phosphoric, hydrochloric, hydrobromic, hydroiodic, sulfamic, citric, lactic, maleic, malic, succinic, tartaric, cinnamic, acetic, benzoic, gluconic, ascorbic and related acids.

The preferred compounds provided by the invention are, with respect to general formula (I), those in which Z is a piperidino group having the formula (A'),

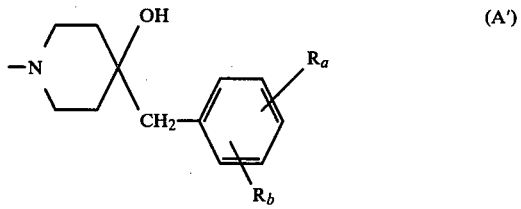

(wherein $R_a$ and $R_b$ are as defined above) or 4-(2'-oxo-1'-benzimidazolinyl)piperidino represented by the formula (B'),

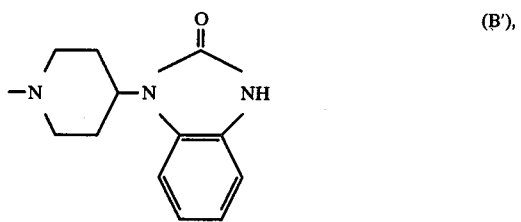

$R^1$ is amino, $C_1$–$C_5$ alkanoylamino, and more preferably acetamino, $C_1$–$C_4$ alkylamino, and more preferably ethylamino, or halogen, and more preferably fluorine or chlorine, and $R^2$ is halogen and more preferably fluorine.

The novel compounds provided by this invention have useful pharmacological and pharmaceutical properties and application in view of their central nervous system depressing activities. More specifically, the compounds provided by the invention are psychotropic, neuroleptic and analgesic agents.

The present inventors studied in order to find an advantageous process in which substituted γ-piperidinobutyrophenone derivative having a substituent at the ortho position can be produced. As a result, the present inventors found a novel and advantageous process for producing various substituted γ-piperidinobutyrophenone derivatives including such ortho-substituted compounds. The most important characteristic of the process of our finding resides in the production of o-acylamino-γ-piperidinobutyrophenone derivatives by the oxidation of 3-γ-piperidinopropylindole derivatives. The acylamino group of the thus obtained o-acylamino-γ-piperidinobutyrophenone derivatives can be converted to unsubstituted or substituted amino group by an ordinary hydrolysis reaction and further subsequently to halogen by an ordinary diazotization and decomposition. Therefore, according to the process of our finding, various γ-piperidinobutyrophenone derivatives can be produced very advantageously.

The compounds of this invention can be prepared by novel processes, which comprises contacting an indole compound of the formula,

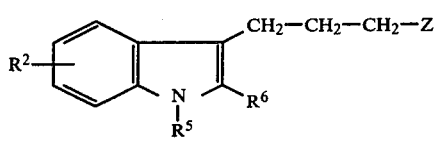 (IX)

wherein each of $R^5$ and $R^6$ is hydrogen or $C_1-C_4$ alkyl and $R^2$ and Z are the same as defined above, with an oxidizing agent to yield a compound of the formula,

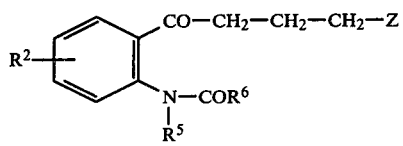 (II)

wherein $R^2$, $R^5$, $R^6$ and Z are the same as defined above, and if necessary, hydrolyzing the resulting compound of the formula (II) to a compound of the formula,

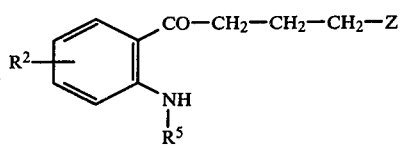 (III)

wherein $R^2$, $R^5$ and Z are the same as defined above, and further diazotizing, if desired, in case $R^5$ is hydrogen, the resulting compound of the formula (III) and subsequently decomposing the resulting diazonium compound to replace the diazonium group by halogen to yield a compound of the formula,

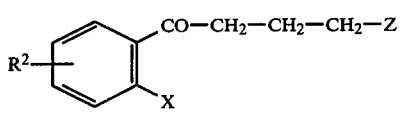 (IV)

wherein X is halogen; and $R^2$ and Z are the same as defined above.

According to the present invention, the objective compound of the formula (I) can be prepared by the process as shown in the following synthetic schema:

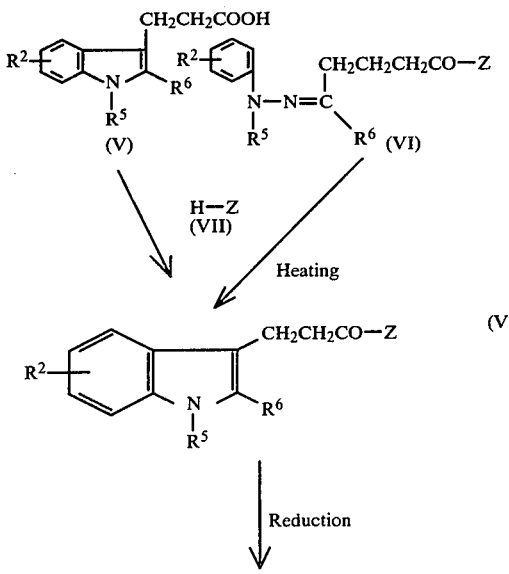

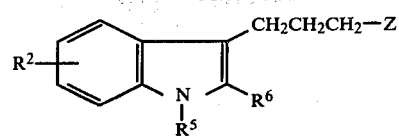 (IX)

Oxidation

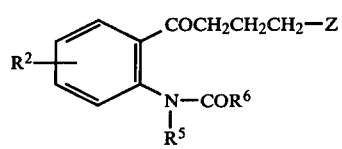 (II)

Hydrolysis

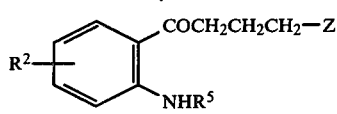 (III)

Diazotization and Replacement

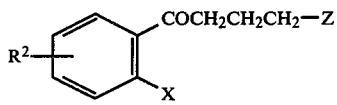 (IV)

wherein $R^2$, $R^5$, $R^6$, Z and X are as identified above.

The 1-[β-(3-indolyl)propionyl]piperidine compounds of the formula (VIII) used as an intermediate in the present invention are prepared by reacting an indolylpropionic acid of the formula (V), or its functionally active derivative such as acid chloride, acid bromide, acid anhydride, mixed acid anhydride, p-nitrophenyl ester and the like, with a piperidine of the formula (VII). The reaction is preferably carried out in the presence of a basic agent or a condensing agent such as pyridine, triethylamine, sodium carbonate, sodium hydroxide, dicyclohexylcarbodiimide and the like in a suitable inert organic solvent such as tetrahydrofuran, ether, dioxane, benzene, toluene, chloroform, dimethylformamide and the like.

The mixed acid anhydride mentioned above include those prepared by treating with ethyl chloroformate, isobutyl chloroformate or the like.

The intermediate compound of the formula (VIII) can also be prepared by heating a phenylhydrazone compound of the formula (VI). The heating is carried out preferably in the presence of an acidic condensing agent such as, for example, hydrogen chloride, sulfuric acid, phosphoric acid, zinc chloride, copper chloride, boron fluoride, polyphosphoric acid and the like in a suitable solvent such as ethanol, isopropanol, tertiary-butanol, acetic acid, benzene, toluene, water and the like.

The compounds of the formula (VIII) thus obtained are converted to the corresponding 3-(γ-piperidinopropyl)indole compounds of the formula (IX) by reacting the former with a reducing agent. A reducing agent such as alkali metal in alcoholic solvent, hydrogen in the presence of a catalyst, metal hydride and the like can be preferably employed. An electrolytic reduction can also be used for the purpose.

It is especially preferable to use metal hydride such as lithium aluminum hydride, diisobutyl aluminum hydride, triisopropyl aluminum hydride, boron hydride or the like, in an inert organic solvent such as, for example, ether, tetrahydrofuran, dioxane, N-ethylmorphorine and the like.

After the reaction is complete, the excess of reducing agent present and the complex compound thereof formed are decomposed by addition of water, an alcohol, ethyl acetate or the like, and then the objective compond (IX) can be isolated or, if necessary, further purified by recrystallization, etc. If desired, the product can be converted into an acid addition salt thereof by treating with a mineral or organic acid. The said salt can be formed with, for example, hydrochloric, sulfuric, phosphoric, hydrobromic, thiocyanic, acetic, propionic, oxalic, citric, malic, tartaric, fumaric, maleic, succinic, glycolic, benzoic, cinnamic, p-aminosalicyclic, salicyclic, methanesulfonic, ascorbic acids, etc.

γ-Piperidinobutyrophenones of the formula (II) can be prepared by contacting the above-obtained 3-γ-piperidinopropylindoles of the formula (IX) or an acid addition salt thereof with an oxidizing agent. In the oxidative cleavage reaction, it is preferred to use an oxidizing agent such as ozone, hydrogen eroxide, performic acid, peracetic acid, perbenzoic acid, chromic acid or potassium permanganate, although the oxidizing agent of the present invention is not limited to the exemplified ones and others may be used.

Generally, the reaction progresses readily at room temperature, but the temperature may be higher or lower if necessary to effect the desired control of the reaction. The oxidizing agent is preferably chromic acid or ozone. The reaction is preferably effected in the presence of a solvent. The choice of solvent depends on the oxidizing agent employed, and is selected from the group consisting of water, acetone, carbon tetrachloride, acetic acid, sulfuric acid and the like. The oxidizing agent is used in stoichiometric amount or more. The reaction temperature varies depending on the oxidizing agent employed.

When the oxidation is carried out by use of chromic acid in the presence of acetic acid, it is preferable that the chromic acid may be used in 2-3 times of the equimolar amount and that the reaction may be carried out at room temperature. A 3-γ-piperidinopropylindole derivative is dissolved or suspended in the solvent and the oxidizing agent is added to the solution or suspension with stirring. Generally, the reaction terminates within about 24 hours.

Where the oxidation is carried out by use of ozone, the reaction is preferably carried out at room temperature. A 3-γ-piperidinopropylindole derivative is dissolved or suspended in a solvent such as formic acid, acetic acid, carbon tetrachloride or the like and ozonized oxygen is bubbled into the solution or suspension with stirring.

The desired γ-piperidinobutyrophenone derivative can be separated from the reaction mixture in a crude form by extraction, with or without prior neutralization, and by evaporation to dryness. The product is further purified, if desired, by recrystallization from a suitable solvent such as ethanol, isopropanol or the like in a standard manner.

The resulting compound of the formula (II) can be hydrolyzed to give the corresponding deacylated compound of the formula (III). The hydrolysis is accomplished under an acidic or alkaline condition according to an ordinary hydrolysis procedure.

γ-Piperidinobutyrophenones of the formula (IV) are prepared by diazotization of the above-obtained o-amino-compound of the formula (III) wherein $R^5$ is hydrogen or an acid addition salt thereof and subsequent treatment of the resulting diazonium salt with a suitable agent to replace the diazonium group by halogen.

The diazotization is performed by a conventional method and the replacement reaction is conducted as follows:

By treating the diazonium salt with copper powder, hydrofluoroboric acid or a metal salt such as cuprous chloride, cuprous bromide, potassium iodide, mercuric halide and the like, there can be obtained γ-piperidinobutyrophenones of the formula (IV).

The following reaction schemes are given in order to exemplify the replacement reaction of the invention.

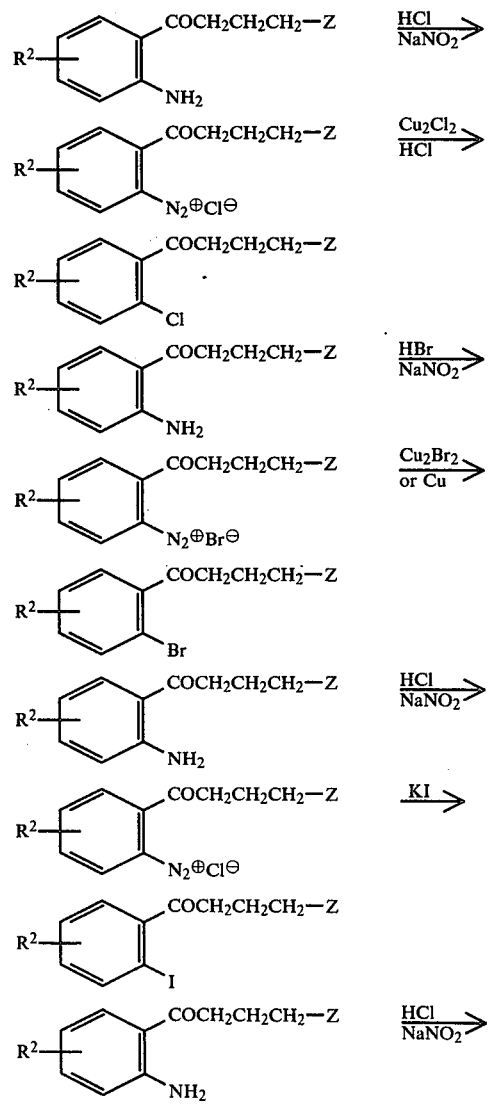

-continued

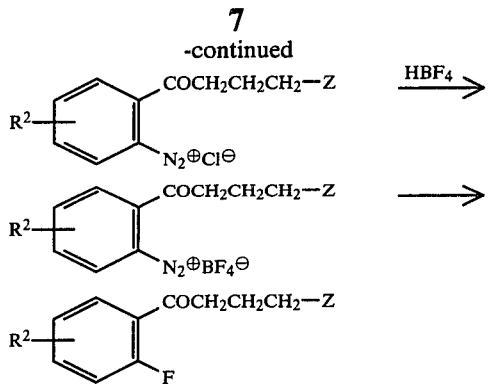

(In the above formulas, R² and Z are the same as described above.)

By the procedure mentioned above, there are synthesized, for example, the following compounds or acid addition salts thereof.

γ-(4-Benzyl-4-hydroxypiperidino)-2-acetamino-4-fluorobutyrophenone
γ-(4-Benzyl-4-hydroxypiperidino)-2-amino-4-fluorobutyrophenone
γ-[4-(4-Chlorobenzyl)-4-hydroxypiperidino]-2-acetamino-5-fluorobutyrophenone
γ-[4-(4-Chlorobenzyl)-4-hydroxypiperidino]-2-amino-5-fluorobutyrophenone
γ-(4-Benzyl-(4-hydroxypiperidino)-2-acetamino-5-fluorobutyrophenone
γ-(4-Benzyl-4-hydroxypiperidino)-2-amino-5-fluorobutyrophenone
γ-[4-Hydroxy-4-(4-methylbenzyl)piperidino]-2-acetamino-4-fluorobutyrophenone
γ-[4-Hydroxy-4-(4-methylbenzyl)piperidino]-2-amino-4-fluorobutyrophenone
γ-[4-Hydroxy-4-(4-methoxybenzyl)piperidino]-2-acetamino-4-fluorobutyrophenone
γ-[4-Hydroxy-4-(4-methoxybenzyl)piperidino]-2-amino-4-fluorobutyrophenone
γ-[4-(3,4-Dichlorobenzyl)-4-hydroxypiperidino]-2-acetamino-4-fluorobutyrophenone
γ-[4-(3,4-Dichlorobenzyl)-4-hydroxypiperidino]-2-amino-4-fluorobutyrophenone
γ-[4-Hydroxy-4-(3-trifluoromethylbenzyl)-piperidino[-2-acetamino-4-fluorobutyrophenone
γ-[4-Hydroxy-4-(3-trifluoromethylbenzyl)-piperidino]-2-amino-4-fluorobutyrophenone
γ-[4-(4-Chlorobenzyl)-4-hydroxypiperidino]-2-(N-ethylacetamino)-4-fluorobutyrophenone
γ-[4-(4-Chlorobenzyl)-4-hydroxypiperidino]-2-ethylamino-4-fluorobutyrophenone
γ-[4-(2-Oxo-1-benzimidazollinyl)piperidino]-2-acetaminobutyrophenone
γ-[4-(2-Oxo-1-benzimidazolinyl)piperidino]-2-aminobutyrophenone
γ-[4-(2-Oxo-1-benzimidazolinyl)piperidino]-2-ethylamino-4-fluorobutyrophenone
γ-[4-(2-Oxo-1-benzimidazolinyl)piperidino]-2-methylamino-4-fluorobutyrophenone
γ-[4-(4-Chlorobenzyl)-4-hydroxypiperidino]-2-methylamino-4-fluorobutyrophenone
γ-(4-Benzyl-4-hydroxypiperidino)-2-chloro-4-fluorobutyrophenone
γ-(4-Benzyl-4-hydroxypiperidino)-2-chloro-5-fluorobutyrophenone
γ-[4-(4-Chlorobenzyl)-4-hydroxypiperidino]-2-chloro-4-fluorobutyrophenone
γ-[4-Hydroxy-4-(4-methylbenzyl)piperidino]-2,4-difluorobutyrophenone
γ-[4-(3,4-Dichlorobenzyl)-4-hydroxypiperidino]-2,4-difluorobutyrophenone
γ-[4-Hydroxy-4-(3-trifluoromethylbenzyl)-piperidino]-2,4-difluorobutyrophenone
γ-[4-(4-Chlorobenzyl)-4-hydroxypiperidino]-2-bromo-4-fluorobutyrophenone
γ-[4-(2-Oxo-1-benzimidazolinyl)piperidino]-2-chloro-5-fluorobutyrophenone
γ-(4-Benzylpiperdino)-2,4difluorobutyrophenone
γ-[4-(4-Chlorobenzyl)piperidino]-2-chloro-4-fluorobutyrophenone
γ-[4-(4Chlorobenzyl)-4-hydroxypiperidino]-2-fluorobutyrophenone
γ-[4-(2-Oxo-1-benzimidazolinyl)piperidino]-2-fluorobutyrophenone
γ-[4-Hydroxy-4-(4-methoxybenzyl)piperidino]-2,4-difluorobutyrophenone The γ-piperidinobutyrophenone compounds thus prepared possess a variety of activities on the central nervous system.

The pharmacological evaluation in laboratory animals demonstrated that they have useful properties as a psychotropic, neuroleptic or analygesic agent.

Some of the compounds of this invention are more effective on anti-apomorphine test or suppression of conditioned avoidance response in rats than chloropromazine.

Other compounds of this invention have strong activity on the acetic acid writhing test in mice.

While the compounds of the present invention have many beneficial activities, they scarecely show any toxic symptoms, and it may safely be said that these compounds are of great value in practical use.

Each of the pharmaceutically active compounds of the invention may be incorporated, e.g. in a tablet as the sole active ingredient for oral administration and may be quite useful as anti-anxiety, anti-psychotonic, anti-emotional, anti-convulsive, anti-psychosis or analgesic drugs. A typical tablet is constituted by from 1 to 2 per cent binder, e.g. tragacanth; from 3 to 10 per cent lubricant, e.g. talcum; from -1.0 per cent lubricant, e.g. magnesium stearate; an average dose of active ingredient; and q.s. 100 per cent of filler, e.g. lactose. The usual oral dosage is 1–100 mg per os daily.

The following examples are given to illustrate the process of the present invention more particularly.

EXAMPLE 1

Step 1

To a stirred solution of 5.0 g of β-(2-methyl-3-indolyl)propionic acid and 2.5 g of triethylamine in 100 ml of chloroform was added dropwise 2.7 g of ethyl chloroformate at a temperature below 0° C. After the addition was complete, stirring was continued for additional 15 minutes and thereto was added 4.7 g of 4-benzyl-4-hydroxypiperidine in several portions. The reaction mixture was stirred for 4 hours at room temperature and allowed to stand overnight. The reaction product was washed thoroughly with water and concentrated to dryness. The residue was recrystallized from ethanol to give 1-[β-(2-methyl-3-indolyl)propionyl]-4-benzyl-4-hydroxypiperidine, melting at 117°–119° C.

Step 2

To a stirred mixture of 2.0 g of lithium aluminum hydride and 50 ml of ether was added dropwise a solution of 4.6 g of 1-[β-(2-methyl-3-indolyl)-propionyl]-4- benzyl-4hydroxypiperidine in 80 ml of tetrahydrofuran over a period of 30 minutes under gentle refluxing.

Stirring and refluxing were continued for additional 4 hours and the reaction mixture was treated gradually with 10 ml of cold water under cooling with ice. The resulting precipitate was filtered off and the filtrate was concentrated to dryness. Recrystallization of the residue from benzene gave 2-methyl-3-[γ-(4-benzyl-4-hydroxypiperidino)propyl]-indole, melting at 132°–134° C.

Step 3

Into a solution of 3.0 g of 2methyl-3-[γ-(4-benzyl-4-hydroxypiperidino)propyl]indole in 50 ml of acetic acid was introduced a stream of oxygen containing about 3% of ozone over a pepiod of 30 minutes during which time the temperature was maintained at 15°–20° C. The resulting solution was diluted with 200 ml of water and made alkaline by slow addition of aqueous sodium hydroxide. The oil matter which was separated was extracted with chloroform and the extract was washed with water, dried and concentrated to give γ-(4-benzyl-4hydroxypiperidino)-2-acetaminobutyrophenone as a viscous liquid. I.R. ν max: 3430, 3250, 1680, 1650, 1520, 1300 (cm$^{-1}$).

The product obtained above was dissolved in 50 ml of ethanol and the resulting solution was heated under reflux with 6 ml of concentrated hydrochloric acid for 2hours. After cooling, the mixture was diluted with 100 ml of water, made alkaline by slow addition of aqueous sodium hydroxide and extracted with ethyl acetate. The extract was washed with water and concentrated to dryness. Recrystallization of the residue from ethanol gave γ-(4-benzyl-4-hydroxypiperidino)-2-aminobutyrophenone, melting at 123°–124° C.

Step 4

To a cooled solution of 3.6 g of γ-(4-benzyl-4-hydroxypiperidino)-2-aminobutyrophenone in 35 ml of 2N hydrochloric acid was added dropwise a solution of 0.74 g of sodium nitrite in 5 ml of water with stirring below 0° C. The resulting diazonium salt solution was added all at once to a cold suspension of 1.5 g of cuprous chloride in 5 ml of concentrated hydrochloric acid with vigorous stirring. The mixture was stirred for 30 minutes under cooling with ice, and stirring was continued for 2 hours at room temperature and then for 1 hour at 55°–60° C. After cooling, the reaction mixture was made alkaline, and extracted with chloroform. The extract was washed with water, dried and concentrated to a residue. The residue was treated with methanolic hydrogen chloride and recrystallization of the resulting solid matter from isopropanol gave γ-(4-benzyl-4-hydroxypiperidino)-2-chlorobutyrophenone hydrochloride.8c

EXAMPLE 2

To a solution of 2.0 g of 2-methyl-3-[γ-(4-p-chlorobenzyl-4-hydroxypiperidino)propyl]-6-fluoroindole (prepared according to a procedure similar to that of steps 1 and 2 of Example 1) in 20 ml of acetic acid was added dropwise a solution of 1.7 g of chromic anhydride in 3 ml of water with stirring below 15° C. The mixture was stirred at room temperature overnight and poured into 120 ml of water. Thereto was added an aqueous solution of sodium hydroxide to make alkaline and the precipitated solid was collected by suction filtration on a Büchner funnel and washed with three 40 ml portions of warm chloroform. The combined washings were washed with water and concentrated to dryness. The residual solid was recrystallized from aqueous acetone to give γ-[4-(p-chlorobenzyl)-4-hydroxypiperidino]-2-acetamino-4-fluorobutyrophenone, which was converted to its hydrochloride by a conventional procedure, m.p. 105°–108° C.

This was hydrolyzed under a condition similar to that of step 3 of Example 1 to yield γ-[4-p-chlorobenzyl)-4-hydroxypiperidino]-2-amino-4-fluorobutyrophenone hydrochloride, m.p. 155°–160° C.

By a method similar to that of Example 1 or 2, the following compounds were obtained.

γ-[4-(2-Oxo-1-benzimidazolinyl)piperidino]-2-acetamino-4-fluorobutyrophenone, m.p. 205°–207.5° C.

γ-[4-(2-Oxo-1-benzimidazolinyl)piperidino]-2-amino-4-fluorobutyrophenone, m.p. 231.5°–234° C.

γ-[4-(2-Oxo-1-benzimidazolinyl)piperidino]-2-chloro-4-fluorobutyrophenone, m.p. 215°–223° C.

γ-[4-(2-Oxo-1-benzimidazolinyl)piperidino]-2,4-difluorobutyrophenone, m.p. 150°–152° C.

γ-(4-Benzyl-4-hydroxypiperidino)-2-acetamino-4-fluorobutyrophenone

γ-(4-Benzyl-4-hydroxypiperidino)-2-aminobutyrophenone hydrochloride

γ-(4-Benzyl-4-hydroxypiperidino)-2-chloro-4-fluorobutyrophenone

γ-(4-Benzyl-4-hydroxypiperidino)-2,4-difluorobutyrophenone hydrochloride, m.p. 164.5°–166.5° C.

γ-[4-(4-Chlorobenzyl)-4-hydroxypiperidino]-2,4-difluorobutyrophenone hydrochloride, m.p. 179.5°–183.5° C.

γ-[4-(2-Oxo-1-benzimidazolinyl)piperidino]-2-acetamino-5-fluorobutyrophenone, m.p. 102°–104.5° C. (decomposition) (containing 1 molecule of ethanol)

γ-[4-(2-Oxo-1-benzimidazolinyl)piperidino]-2-amino-5-fluorobutyrophenone, m.p. 183°–183.5° C.

γ-[4-(2-Oxo-1-benzimidazolinyl)piperidino]-3-fluorobutyrophenone, m.p. 163.5°–164.5° C.

γ-[4-(2-Oxo-1-benzimidazolinyl)piperidino]-2-ethylamino-4-fluorobutyrophenone

γ-[4-(4-Chlorobenzyl)-4-hydroxypiperidino]-2-ethylamino-4-fluorobutyrophenone hydrochloride γ-[4-Hydroxy-4-(4-methylbenzyl)piperidino]-4-fluorobutyrophenone, m.p. 90° C.

γ-[4-Hydroxy-4-(4-methoxybenzyl)piperidino]-4-fluorobutyrophenone hydrochloride, m.p. 175° C.

γ-[4-Hydroxy-4-(β-phenethyl)piperidino]-4-fluorobutyrophenone hydrochloride, m.p. 180° C.

What is claimed is:

1. A compound of the formula,

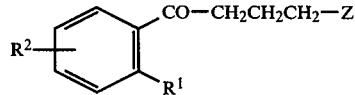

wherein
R$^1$ is halogen, amino, C$_1$–C$_5$ alkanoylamino, C$_1$–C$_4$ alkylamino or N-(C$_1$–C$_5$-alkanoyl)C$_1$–C$_4$ alkylamino;
R$^2$ is hydrogen or halogen, provided that when R$^1$ is halogen, R$^2$ must be halogen; and
Z is a piperidino group having the formula (A′),

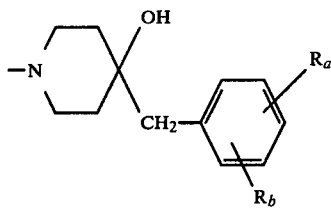

(wherein each of $R_a$ and $R_b$ is hydrogen, halogen, $C_1-C_4$ alkyl, $C_1-C_4$ alkoxy or trifluoromethyl) or a piperidino group having the formula (B')

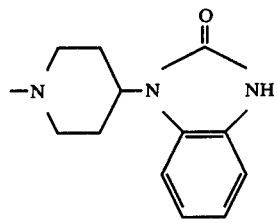

provided that when $R^1$ is amino and $R^2$ is hydrogen, Z cannot be represented by the formula (A'), and a pharmaceutically acceptable acid addition salt thereof.

2. A compound according to claim 1, wherein $R^1$ is halogen.

3. A compound according to claim 1, wherein $R^1$ is amino, acetamino or ethylamino.

4. A compound of the formula,

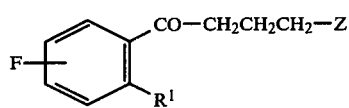

wherein
$R^1$ is halogen, amino, $C_1-C_5$ alkanoylamino, $C_1-C_4$ alkylamino or N-($C_1-C_5$-alkanoyl)$C_1-C_4$ alkylamino and
Z is a piperidino group having the formula (A'),

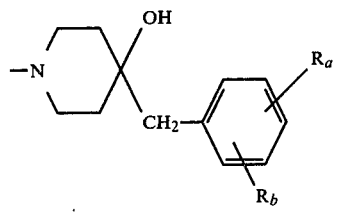

(wherein each of $R_a$ and $R_b$ is hydrogen, halogen, $C_1-C_4$ alkyl, $C_1-C_4$ alkoxy or trifluoromethyl) or a piperidino group having the formula (B'),

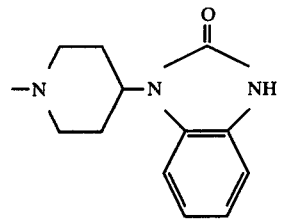

and a pharmaceutically acceptable acid addition salt thereof.

5. A compound according to claim 4, wherein $R^1$ is halogen.

6. A compound according to claim 4, wherein $R^1$ is amino, acetamino or ethylamino.

7. A compound of the formula,

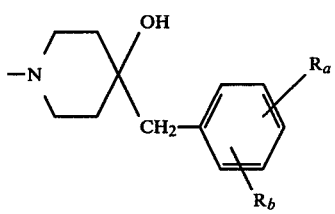

wherein
$R^1$ is halogen, amino, $C_1-C_5$ alkanoylamino, $C_1-C_4$ alkylamino or N-($C_1-C_5$-alkanoyl)$C_1-C_4$ alkylamino; and
Z is a piperidino group of the formula (A'), (A')

(wherein each of $R_a$ and $R_b$ is hydrogen, halogen, $C_1-C_4$ alkyl, $C_1-C_4$ alkoxy or trifluoromethyl) or a piperidino group having the formula (B'), (B'), and a pharmaceutically acceptable acid addition salt thereof.

8. γ-[4-(4-Chlorobenzyl)-4-hydroxypiperidino]-2-acetamino-4-fluorobutyrophenone and its hydrochloride.
9. γ-[4-(4-Chlorobenzyl)-4-hydroxypiperidino]-2-amino-4-fluorobutyrophenone and its dihydrochloride.
10. γ-[4-(4-Chlorobenzyl)-4-hydroxypiperidino]-2,4-difluorobutyrophenone and its hydrochloride.
11. γ-(4-Benzyl-4-hydroxypiperidino)-2,4-difluorobutyrophenone and its hydrochloride.
12. γ-[4-(2-Oxo-1-benzimidazolinyl)piperidino]-2-acetamino-4-fluorobutyrophenone.
13. γ-[4-(2-Oxo-1-benzimidazlinyl)piperidino]-2-amino-4-fluorobutyrophenone and its hydrochloride.
14. γ-[4-(2-Oxo-1-benzimidazolinyl)piperidino]-2,4-difluorobutyrophenone.
15. γ-(4-Benzyl-4-hydroxypiperidino)-2-aminobutyrophenone.

* * * * *